(12) United States Patent
Johnson

(10) Patent No.: US 9,284,668 B2
(45) Date of Patent: Mar. 15, 2016

(54) CONTINUOUS BRAIDED CLOSED LOOP IMPLANT

(71) Applicant: Medos International Sàrl, Le Locle (CH)

(72) Inventor: Stephen Johnson, Johnston, RI (US)

(73) Assignee: MEDOS INTERNATIONAL SÁRL, Le Locle (CH)

( * ) Notice: Subject to any disclaimer, the term of this patent is extended or adjusted under 35 U.S.C. 154(b) by 455 days.

(21) Appl. No.: 13/828,407

(22) Filed: Mar. 14, 2013

(65) Prior Publication Data

US 2014/0277122 A1 Sep. 18, 2014

(51) Int. Cl.
*D04C 1/12* (2006.01)
*A61B 17/04* (2006.01)
*A61B 17/06* (2006.01)
*A61B 17/00* (2006.01)

(52) U.S. Cl.
CPC .............. *D04C 1/12* (2013.01); *A61B 17/0401* (2013.01); *A61B 17/06166* (2013.01); *A61B 2017/00526* (2013.01); *A61B 2017/0404* (2013.01); *A61B 2017/044* (2013.01); *A61B 2017/0406* (2013.01); *A61B 2017/0445* (2013.01)

(58) Field of Classification Search
CPC .............. D04C 1/12; D04C 3/48; D04C 7/00; A61B 17/0401; A61B 17/06166
USPC ...................... 87/7, 34; 57/21, 201
See application file for complete search history.

(56) References Cited

U.S. PATENT DOCUMENTS

| 4,792,336 | A | * | 12/1988 | Hlavacek et al. | .......... 623/13.18 |
| 4,959,069 | A | | 9/1990 | Brennan et al. | |
| 5,306,301 | A | | 4/1994 | Graf et al. | |
| 6,193,754 | B1 | | 2/2001 | Seedhom | |
| 6,352,603 | B1 | | 3/2002 | Bryant | |
| 7,658,751 | B2 | * | 2/2010 | Stone et al. | .................... 606/232 |
| 8,118,836 | B2 | * | 2/2012 | Denham et al. | ................ 606/232 |
| 8,652,171 | B2 | * | 2/2014 | Stone et al. | .................... 606/232 |
| 8,926,662 | B2 | * | 1/2015 | Perriello et al. | ............... 606/232 |
| 8,932,331 | B2 | * | 1/2015 | Kaiser et al. | .................... 606/232 |
| 8,936,621 | B2 | * | 1/2015 | Denham et al. | ................ 606/232 |
| 2010/0191319 | A1 | * | 7/2010 | Lilburn et al. | ................ 623/1.15 |
| 2011/0265908 | A1 | * | 11/2011 | Clerc et al. | .................. 140/71 R |

* cited by examiner

*Primary Examiner* — Shaun R Hurley

(57) ABSTRACT

Devices and systems for use in soft tissue repair are provided, as are methods of manufacturing the same. In one exemplary embodiment, an implantable surgical construct includes an implant and a continuous braided closed filament loop that is attached to the implant. The continuous loop can be formed from a single strand of filament such that portions of the filament, sometimes referred to as tails, can be arranged with respect to each other to form a braided configuration. A related method of manufacture can involve passing portions of a single strand of filament around different sets of posts and selectively over and under each other to create the braided configuration. Other devices, systems, and methods of manufacturing are also provided, including some that involve using multiple strands of suture to form a continuous braided closed filament loop.

20 Claims, 8 Drawing Sheets

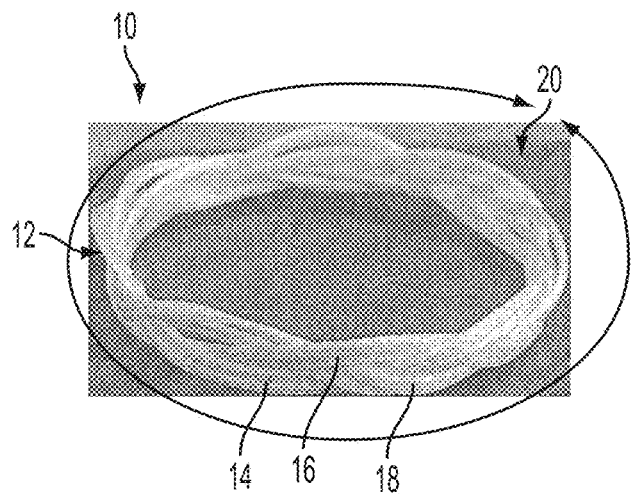
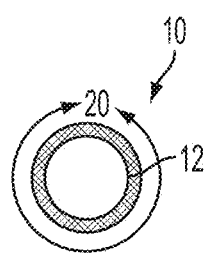
FIG. 1A
FIG. 1B
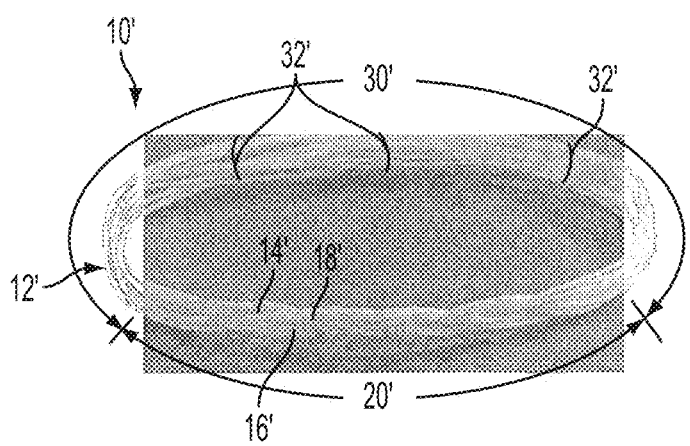
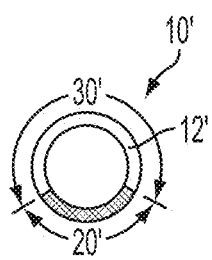
FIG. 2A
FIG. 2B

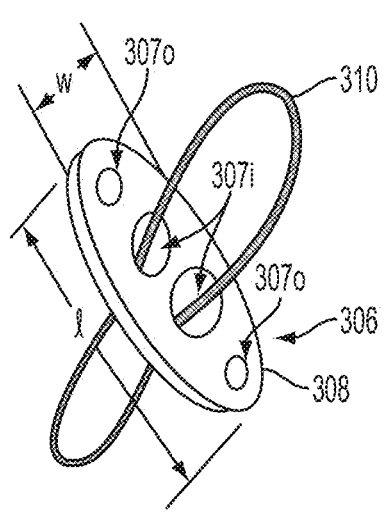
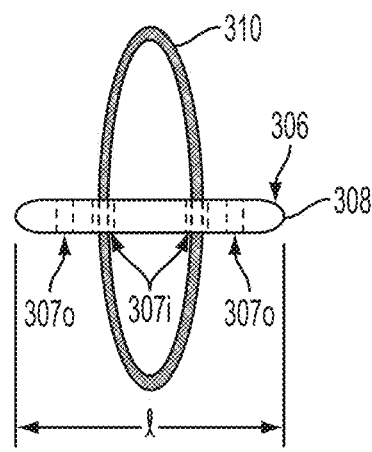
FIG. 5A  FIG. 5B
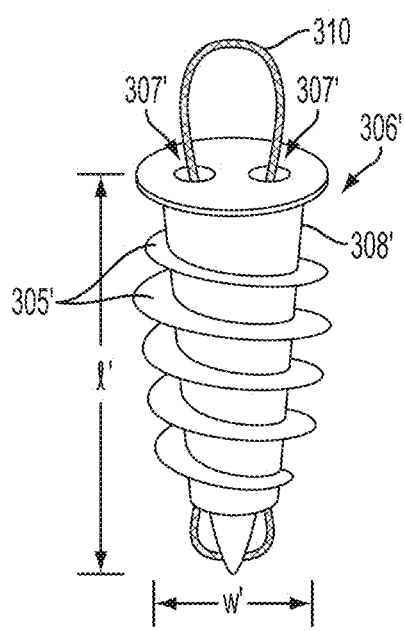
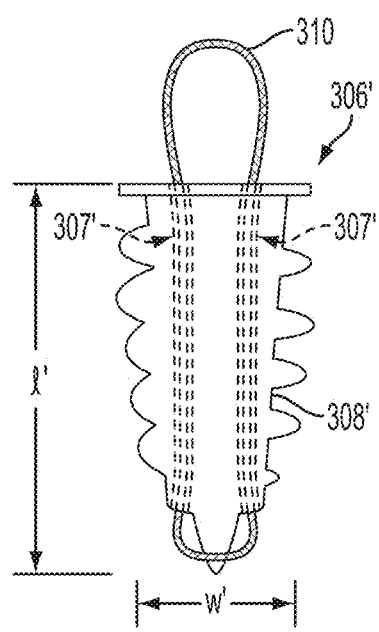
FIG. 6A  FIG. 6B

CONTINUOUS BRAIDED CLOSED LOOP IMPLANT

FIELD

The present disclosure relates to devices and systems for securing soft tissue to bone, as well as methods of manufacturing the same. More particularly the devices, systems, and methods relate to implants having a continuous closed loop that includes a braided configuration.

BACKGROUND

A common injury, especially among athletes and people of advancing age, is the complete or partial detachment of tendons, ligaments, or other soft tissues from bone. Tissue detachment may occur during a fall, by overexertion, or for a variety of other reasons. Surgical intervention is often needed, particularly when tissue is completely detached from its associated bone. Currently available devices for tissue attachment include screws, staples, suture anchors, and tacks, at least some of which are used in conjunction with suture to perform repair procedures.

Suture used in conjunction with repair devices can come in a variety of configurations, for instance in a braided configuration. Typically, braided sutures are created on a braider using eight or sixteen filaments. In order to create a continuous closed loop having a braided configuration, however, typically two ends of suture are tied or otherwise connected together. Braiders are not configured to create continuous braided closed loops. In some instances, a continuous braided closed loop may be able to be formed manually by taking at least three separate filaments and alternately crossing them over each other so that a braid results and the filaments can be manipulated to form a loop shape. In such instances, a person continues to manually weave the filaments back and forth until a desired length, pattern, and thickness are achieved. The formation of a continuous closed loop having a braided configuration is thus time consuming, and can be susceptible to imperfections from user error due to each weave being performed manually. Additionally, as the number of filaments used to form the braided configuration increases, so too can the risk of failure due to unsatisfactory filament. Still further, the use of separate filaments can increase costs and become difficult to manage during the construction of the braided suture.

Another suture configuration that can be used in conjunction with tissue repair devices is a closed loop configuration. The closed loop can provide stability and strength in certain repair procedures. Some closed loops can also be braided. To the extent closed loops are braided, they can suffer from the same deficiencies as a braided suture generally. Additionally, existing types of closed loop configurations can be deficient because they can be difficult to manufacture in a fast and efficient manner while maintaining a desired strength.

Accordingly, it is desirable to provide devices and systems, and methods of manufacturing the same, making it easy to create continuous braided closed loop implants. The implants can be easier and possibly less expensive to manufacture, without sacrificing the strength and integrity of the implant. In some instances, it can also be desirable to form continuous braided closed loop implants from a minimum number of filaments, including as little as a single, elongate filament.

SUMMARY

Devices and systems for creating a surgical implant that includes a continuous braided closed filament loop are generally provided, as are methods of manufacturing the same. In one exemplary embodiment an implantable surgical construct includes an implant having a body with a first thru-hole formed therein and a continuous braided closed filament loop. The loop can have an attachment portion attached to the implant through the first thru-hole and a free portion that extends from the implant. The closed filament loop can be configured to be formed from a single strand of filament having at least three tails such that a second tail is passed under a first tail a plurality of times and a third tail is passed between the first and second tails a plurality of times.

The implant to which the closed filament loop is attached can be a suture anchor. In some embodiments, the implant can have a length that is greater than a width, as can be the case with implants like cortical buttons. The implant can include more than one thru-hole formed therein, with a second thru-hole being spaced a distance apart from the first thru-hole.

In some embodiments, the construct can have multiple closed filament loops. Each loop can be formed from a single strand of filament having at least three tails. Thus, if four loops are included with the construct, four filaments can be used to form the implant—one filament per loop. In one embodiment, the construct can include at least one additional continuous braided closed filament loop having an attachment portion attached to the implant and a free portion that extends from the implant. The additional continuous loop can be attached through a second thru-hole of the implant. Similar to the first loop, the second closed filament loop can be configured to be formed from a single strand of filament having at least three tails such that a second tail is passed under a first tail a plurality of times and a third tail is passed between the first and second tails a plurality of times.

Embodiments that include two or more continuous braided closed filament loops can have various configurations for the various loops. For example, the loops can have approximately the same loop diameter. By way of further example, the single filament used to form one loop can be visually identical to the single filament used to form the second loop. Alternatively, the single filament used to form one loop can be visually distinct to the single filament used to form the second loop.

The distribution of portions of the loop that are braided and portions that are not braided can vary for different loops. In one exemplary embodiment, at least one-quarter of the circumference of the continuous braided closed filament loop has a continuous braided configuration formed by first, second, and third tails of the suture, and at least one-quarter of the circumference of the continuous braided closed filament loop has a straight configuration such that the first, second, and third tails of the suture extend a continuous length without being braided together.

One exemplary method of manufacturing an implantable surgical connector loop can be performed using a single strand of filament. The method can include passing a first tail of the single strand of filament around a first set of posts on a mandrel, passing that first tail around a second set of posts on the mandrel, and passing that first tail around a third set of posts on the mandrel. A leading end of the first tail can be fixedly secured to a portion of the single strand of filament before the portion is passed around the first set of posts a first time such that a continuous braided loop is formed. The posts of each of the first, second, and third sets can be arranged in a pattern such that adjacent posts are opposite and staggered from one another and the filament changes direction as it passes around each post. As the first tail is passed around the second set of posts, a second tail of the same single strand of filament can pass around the first set of posts on the mandrel and can be disposed under the first tail when the first and second tails intersect. As the first tail is passed around the third set of posts, the second tail can pass around the second set of posts and a third tail of the same single strand of filament can pass around the first set of posts. The third tail can be woven between the first and second tails in an alternating over-under pattern to form a braid. Further, the first tail can be passed through at least one thru-hole formed in a surgical implant when moving from the first set of posts to the second set of posts and when moving from the second set of posts to the third set of posts such that the continuous braided closed loop is coupled to the surgical implant.

In some embodiments, the method of manufacturing can include actuating mechanical components associated with the mandrel to automatically repeat the steps of passing the first tail around the first, second, and third sets of posts, thereby increasing a thickness of the continuous braided closed loop. Actuating mechanical components can include rotating at least one roller to slidably move the single strand of suture relative to the first, second, and third sets of posts. Alternatively, or additionally, actuating mechanical components can include rotating the first, second, and third sets of posts to help move the single strand of suture relative to the implant.

Another exemplary method of manufacturing an implantable surgical connector loop can be performed using three strands of filament. The method can include passing a first strand of filament around a first set of posts on a mandrel, passing a second strand of filament around a second set of posts on the mandrel, and passing a third strand of filament around a third set of posts on the mandrel. The posts of each of the first, second, and third sets can be arranged in a pattern such that adjacent posts are opposite and staggered from one another and the respective filament changes direction as it passes around each post. The second strand of filament can be disposed over the first strand of filament when the first and second strands intersect, and the third strand of filament can be woven between the first and second strands of filament in an alternating over-under pattern to form a continuous braided closed loop. Further, a leading end of the first strand of filament can be fixedly secured to a mid-portion of the first strand of filament to form a first closed loop disposed around the mandrel. Likewise, a leading end of the second strand of filament can be fixedly secured to a mid-portion of the second strand of filament and a leading end of the third strand of filament can be fixedly secured to a mid-portion of the third strand of filament to form a second closed loop disposed around the mandrel and a third closed loop disposed around the mandrel, respectively. Additionally, the first, second, and third strands of filament can each be passed through one or more thru-holes formed in a surgical implant such that the continuous braided closed loop is coupled to the surgical implant. In some embodiments, the first, second, and third strands can each be passed through the same thru-holes formed in the surgical implant. In other embodiments, the first strand can be passed through a different thru-hole than at least one of the second strand and third strand.

The method of manufacturing can also include actuating mechanical components associated with the mandrel to automatically repeat the steps of passing the first, second, and third strands of filament to increase a thickness of the continuous braided closed loop. Actuating mechanical components can include rotating at least one roller to slidably move the first, second, and third strands of filament relative to the first, second, and third sets of posts. Alternatively, or additionally, actuating mechanical components can include rotating the first, second, and third sets of posts to help move the first, second, and third strands relative to the implant. The first, second, and third strands of filament can be advanced circumferentially around the mandrel a plurality of times.

BRIEF DESCRIPTION OF DRAWINGS

This invention will be more fully understood from the following detailed description taken in conjunction with the accompanying drawings, in which:

FIG. 1A is a perspective view of one exemplary embodiment of a continuous braided closed loop implant;

FIG. 1B is a side view of the implant of FIG. 1A;

FIG. 2A is a perspective view of another exemplary embodiment of a continuous braided closed loop implant;

FIG. 2B is a side view of the implant of FIG. 2A;

FIG. 5A is a perspective view of one exemplary embodiment of a surgical construct having a continuous braided closed loop attached to an implant;

FIG. 5B is a side view of the surgical construct of FIG. 5A;

FIG. 6A is perspective view of another exemplary embodiment of a surgical construct having a continuous braided closed loop attached to an implant;

FIG. 6B is a side view of the surgical construct of FIG. 6A;

DETAILED DESCRIPTION

Figure 3A:
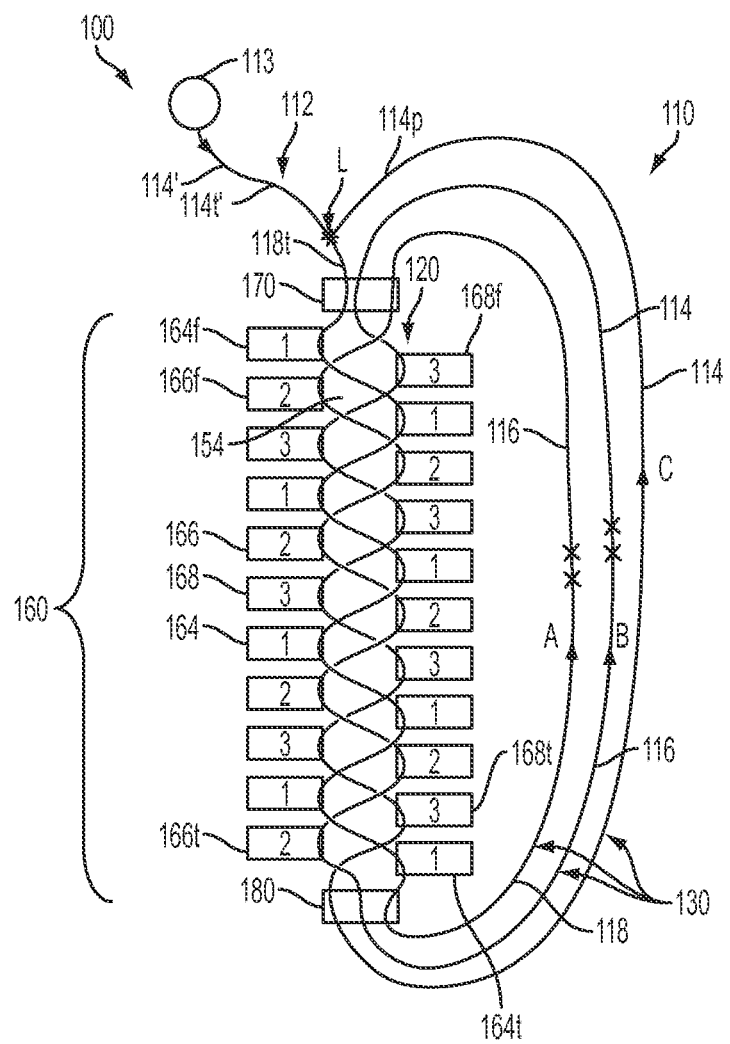
FIG. 3A is a schematic view of one exemplary embodiment of a set-up for use in manufacturing a continuous braided closed loop implant from a single strand of filament.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention. By way of non-limiting example, features described with respect to forming a surgical construct using a single suture filament can generally be applied to surgical constructs formed using a plurality of suture filaments. Further, in the present disclosure, like-numbered components of the embodiments generally have similar features. Still further, sizes and shapes of the systems and devices, and the components thereof, can depend at least on the anatomy of the subject in which the systems and devices will be used, the size and shape of components with which the systems and devices will be used, and the methods and procedures in which the systems and devices will be used.

The figures provided herein are not necessarily to scale. Further, to the extent arrows are used to describe a direction a component can be tensioned or moved, these arrows are illustrative and in no way limit the direction the respective component can be tensioned or moved. A person skilled in the art will recognize other ways and directions for creating the desired tension or movement. Additionally, a number of terms may be used throughout the disclosure interchangeably but will be understood by a person skilled in the art. By way of non-limiting example, the terms "suture" and "filament" may be used interchangeably.

The present disclosure generally relates to surgical devices or constructs that include a continuous braided closed loop. The continuous braided closed loop can be its own implantable device or construct, or it can be coupled to another implantable component, such as a surgical anchor or cortical button, to form an implantable device or construct. In some exemplary embodiments, the continuous braided closed loop is formed from a single strand of filament. In such instances, portions of the single strand, sometimes referred to as tails, can be manipulated with respect to each other to form a braided configuration. For example, the single strand of filament can have three tails, with a braided configuration resulting from passing a second tail under a first tail a plurality of times and a third tail between the first and second tails a plurality of times. In other exemplary embodiments, the continuous braided closed loop is formed from multiple suture filaments. In such instances, each filament can be manipulated with respect to the others to form a braided configuration. For example, a braided configuration can result from passing a second filament under a first filament a plurality of times and a third filament between the first and second filaments a plurality of times.

The disclosure also relates to manufacturing methods for forming continuous braided closed loops and other devices or constructs that incorporate one or more such loops. The methods can be used to create a braided configuration from a single suture filament or from multiple suture filaments. The methods can include automated portions such that once a path for the braided configuration is manually set by the user, further passes along the path can be carried out in an automated manner, i.e., without further manual braid formation by the user.

FIGS. 1A and 1B illustrate one exemplary embodiment of a continuous braided closed loop 10 formed using methods described herein. As shown, the loop 10 is formed from a single strand of filament 12 and has a braided configuration 20 formed along a substantial majority of the circumference of the loop 10. The remaining portion of the loop 10 can be referred to generally as a straight configuration. For purposes of describing the filament 12 and the formation of the braided configuration 20, the filament can have three distinct portions or tails 14, 16, 18 that repeat consecutively along a length of the filament 12. Thus, when the filament 12 is extended in an approximate straight line, a second portion or tail 16 follows a first portion or tail 14, a third portion or tail 18 follows the second portion or tail 16, another first portion or tail 14 follows the third portion or tail 18, and so forth until the length of the filament 12 terminates. In some embodiments each portion or tail 14, 16, 18 can be approximately the same length, which can make braiding them together easier.

The respective first, second, and third tails 14, 16, 18 can be manipulated with respect to each other to form the braided configuration 20. In the illustrated embodiment, a plurality of first tails 14 is disposed over a plurality of second tails 16, and a plurality of third tails 18 is woven between the first and second tails 14, 16. As the number of first, second and third tails 14, 16, 18 increases, so too does the thickness of the loop 10.

In an alternative embodiment, shown in FIGS. 2A and 2B, a continuous braided closed loop 10' having a braided configuration 20' that does not extend for a substantial majority of the loop's circumference. As shown, more than one-quarter but less than one-half of the loop 10' has a braided configuration, while the remaining portion of the loop 10' has a generally straight configuration 30'. Similar to the loop 10, the continuous braided closed loop 10' is formed from a single strand of filament 12', and portions or tails 14', 16', 18' thereof are woven with respect to each other to form the braided configuration 20'. In the illustrated embodiment, first, second, and third tails 14', 16', 18' are manipulated with respect to each other in the same manner as described with respect to the loop 10, except a smaller portion of each tail 14', 16', 18' is used to form the braided configuration 20' and a larger portion of each tail 14', 16', 18' is used to form the generally straight configuration 30'.

As shown, the portion of the continuous braided closed loop 10' that has the generally straight configuration 30' includes lengths of the first, second, and third tails 14', 16', 18' running substantially parallel to each other. The tails 14', 16', 18' can be bunched together and can cross each other in some instances, but they are not generally woven together to form a braid or similar configuration. In some embodiments one or more braces 32' can be disposed around the tails 14', 16', 18' that form the generally straight configuration 30' to help keep the tails 14', 16', 18' relatively compact with respect to each other.

Each of the loop 10 and the loop 10' can be used alone as a surgical implant. More typically, both the loop 10 and the loop 10' can be used in conjunction with other implants, such as suture anchors and cortical buttons, as described in greater detail below. A person skilled in the art will understand how to use the loops 10, 10' to attach soft tissue to bone, regardless of whether the loops 10, 10' are attached to other implants.

The type, size, and strength of the filament 12, 12' used to form the loops 10, 10' can depend, at least in part, on any other materials used in conjunction with the loops, including any material(s) of a suture anchor, cortical button, or other type of implant, the desired configuration of the continuous braided closed loop, and the type of procedure in which it is used. In one exemplary embodiment the filament is a #0 filament (about 26 gauge to about 27 gauge), such as an Orthocord™ filament that is commercially available from DePuy Mitek, LLC., 325 Paramount Drive, Raynham, Mass. 02767, or an Ethibond™ filament that is commercially available from Ethicon, Inc., Route 22 West, Somerville, N.J. 08876. The thickness of the filament should provide strength in the connection but at the same time minimize the trauma caused to tissue through which it passes. In some embodiments the filament can have a size in the range of about a #5 filament (about 20 gauge to about 21 gauge) and about a #4-0 filament (about 32 gauge to about 34 gauge). Orthocord™ suture is approximately fifty-five to sixty-five percent PDS™ polydioxanone, which is bioabsorbable, and the remaining thirty-five to forty-five percent ultra high molecular weight polyethylene, while Ethibond™ suture is primarily high strength polyester. The amount and type of bioabsorbable material, if any, utilized in the filaments of the present disclosure is primarily a matter of surgeon preference for the particular surgical procedure to be performed. In still other embodiments, the filament can be formed from a thinner filament, for instance a filament used to form Orthocord™ and Ethibond™ filaments. In some embodiments, the thinner filament can have a linear mass density of fibers in the range of about 55 decitex to about 440 decitex, and in one exemplary embodiment the thinner filament can have a linear mass density of fibers of about 110 decitex. The thinner filaments can be made from a variety of materials, including but not limited to an ultra high molecular weight material or polyester.

In some exemplary embodiments, a length of the filament 12, 12' can be in the range of about 0.5 meters to about 2.5 meters, and in one embodiment it has a length of about 1 meter. A person skilled in the art will recognize that filaments of this length can be formed into a variety of different configurations depending on the desired diameter and thickness of the continuous braided closed loop. Thus, in some embodiments, a diameter of the continuous braided closed loop 10, 10' can be in the range of about 10 millimeters to about 70 millimeters, and in one embodiment has a diameter of about 30 millimeters, while a thickness of the loop 10, 10' can be in the range of about 5 millimeters to about 30 millimeters, and in one embodiment has a thickness of about 10 millimeters. In embodiments in which a single strand of filament is used to form the continuous braided closed loop, the filament can be divided into any number of portions or tails for purposes of forming the braided configuration, but in some exemplary embodiments the filament can be divided between about three tails and about twelve tails, and more particularly between about three tails and about six tails. A person skilled in the art will recognize different types of braid configurations that can be formed from any number of tails in view of the present disclosure, and that such configurations do not depart from the spirit of the present disclosure.

As discussed below, in some embodiments, multiple filaments can be used to form the continuous braided closed loop rather than multiple tails of a single filament. The types of filaments that can be used in such embodiments can be similar to those discussed above with respect to a single strand of filament. The dimensions of the resulting continuous braided closed loop, i.e., the diameter and the thickness, can also be similar. The length of each filament used to form the closed loop, however, can typically be less than the lengths when only one filament is used to form the loop. Thus, in some embodiments, a length of each separate filament used to form the loop can be in the range of about 0.2 meters to about 0.8 meters, and in one embodiment each separate filament can have a length of about 0.4 meters.

Figure 3B:
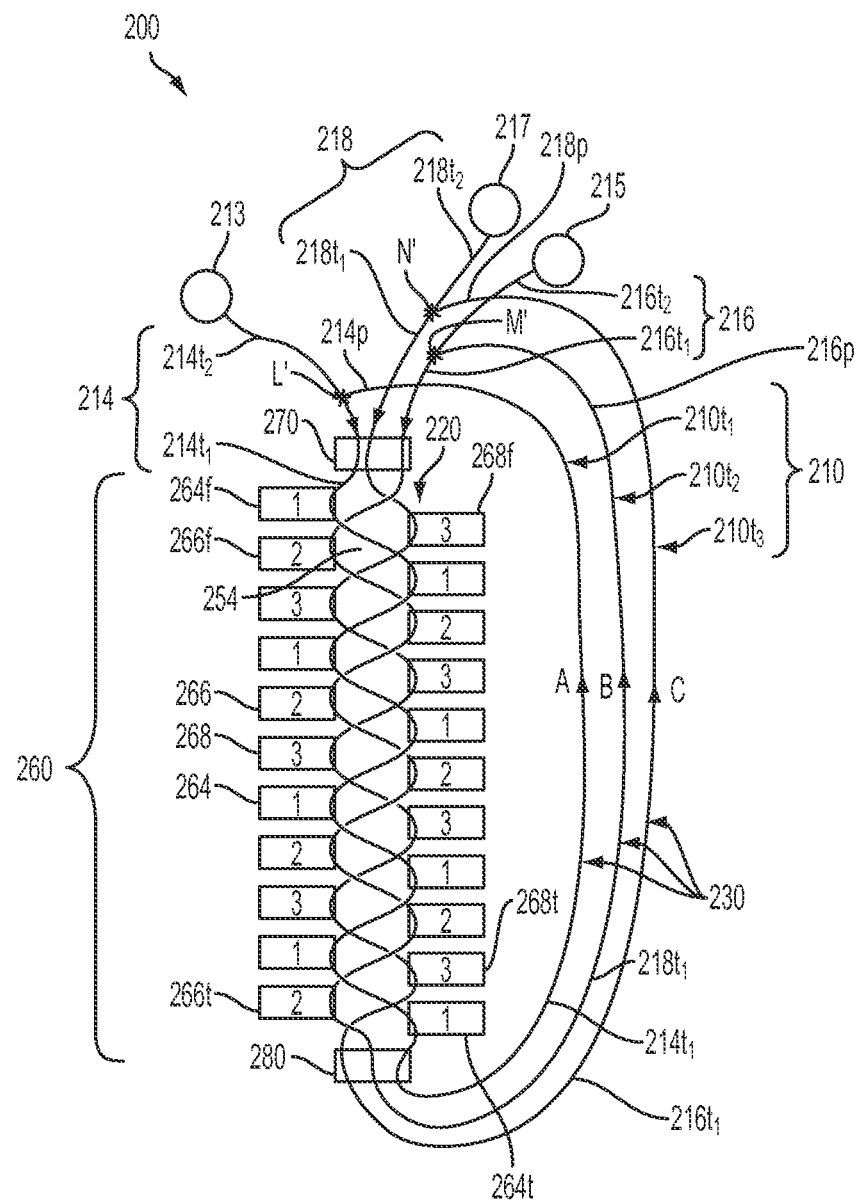
FIG. 3B is a schematic view of one exemplary embodiment of a set-up for use in manufacturing a continuous braided closed loop implant from three strands of filament.

Now turning to methods of manufacturing continuous braided closed loops such as the loops 10, 10', a number of different techniques and machines can be used to form the loops. These types of techniques are first described schematically, as shown in FIGS. 3A and 3B, and then are described with respect to a set-up for manufacturing the continuous braided closed loops, as shown in FIGS. 4A-4B, 7A-7B, 8A-8B, and 9A-9B. The schematic descriptions begin by first describing a method of manufacturing a continuous braided closed loop using a single filament, as shown in FIG. 3A, and then describing a method of manufacturing a continuous braided closed loop using three separate filaments, as shown in FIG. 3B.

FIG. 3A schematically illustrates one exemplary embodiment of a system 100 for forming a continuous braided closed loop 110 using a single filament 112. The system 100 can generally include a plurality of pins or posts 160 disposed on a surface 154 and a suture filament 112 that is selectively passed around the posts 160 to form the continuous braided closed loop 110. As shown, the posts 160 can be divided into a first set of posts 164 (each displaying the numeral "1"), a second set of posts 166 (each displaying the numeral "2"), and a third set of posts 168 (each displaying the numeral "3"), with adjacent posts in the same set being opposite and staggered from one another. In the illustrated embodiment, the posts 160 are schematically represented by rectangles, but in practice the rectangles can be actual pins or posts capable of receiving filament for forming loops. Accordingly, while in the illustration it may look like the filament 112 is touching or passing through an inner portion of the rectangles, this schematic can be representative of the filament 112 passing around the posts 160. Various configurations of the posts 160, and methods by which a filament can be associated therewith, are described in further detail below.

In some embodiments, each set of posts 164, 166, 168 can be distinguishable from the other sets of posts by visual identifiers. For example, each set of posts 164, 166, 168 can be a different color so that a user easily knows which downstream post is the next post in the set of posts. Further, in some embodiments, tails 114, 116, 118 of the filament 112 can be visually distinguishable, providing an alternative or additional way for a user to know which tail should be wrapped around which posts. In one exemplary embodiment, the first set of posts 164 can be predominantly blue, the second set of posts 166 can be predominantly red, and the third set of posts 168 can be predominantly green, while each first tail 114 can be predominantly blue, each second tail 116 can be predominantly red, and each third tail 118 can be predominantly green. Such an embodiment can assist a user in knowing which portions or tails of the filament 112 should be associated with which posts 160 at certain intervals of the method. In other embodiments, it may be desirable for the continuous braided closed loop 110 to have the same color throughout, and thus there may be no visual distinguishing characteristics associated with the filament. A person skilled in the art will recognize other visual and tactile characteristics that can be associated with the posts and/or tails to assist a user in distinguishing portions of the system, including but not limited to coating the differently numbered tails with different textures, or modifying the size of the tails to make them distinct from each other.

The single filament can be stored or located using any number of components known to those skilled in the art for holding a filament before having that filament introduced to the pins or posts. In one exemplary embodiment, the filament 112 is located on a spool 113 prior to being introduced to the posts 160.

The system 110 can include an implant 180, such as an anchor or cortical button, through which the filament 112 can be drawn to mate the resulting loop 110 with the implant 180. In the illustrated embodiment, the implant 180 is disposed downstream from the last post. Optionally, at a location upstream from the first post, the system can include a component 170 to help manage filament. At least because the figures schematically represent exemplary embodiments for forming a continuous braided closed loop 110, the illustrated locations at which the filament 112 pass through each of the implant 180 and the filament management component 170 do not necessarily reflect actual locations where the filament 112 may pass through these components. Rather, the filament 112 can pass through any hole formed in the implant 180 or the filament management component 170, and as the filament 112 passes through either the hole in the implant or the filament management component multiple times, the different passes can be made through the same or different holes formed in each component. In alternative embodiments, the implant 180 can be located upstream from the first post and the filament management component 170 can be located downstream of the last post. Additionally, while in the illustrated embodiment the loop 110 is associated with an implant 180, in other embodiments the loop 110 is used without an implant, or alternatively, the loop 110 is attached to multiple implants, for instance by being disposed between two suture anchors.

In use, a first portion or tail 114 of the filament 112 can be advanced from the spool 113, through the filament management component 170, and to a first post 164f of the first set of posts 164. The first tail 114 can be wrapped around at least a portion of the post 164f, meaning that the tail 114 passes around an outside portion of the post 164f, as shown in later embodiments (FIGS. 4B, 7B, 8B, and 9B). The first tail 114 can then be passed around downstream posts of the first set of posts 164, each downstream post being on a side opposite the previous post of the set. Once the first tail 114 is wrapped around a last post 164t of the first set of posts 164, it can be passed through a thru-hole of the implant 180 (assuming an implant is to be used) and then passed in a direction A, back toward the filament management component 170.

The first tail 114 can then be passed through the filament management component 170 and wrapped around a first post 166f of the second set of posts 166. Subsequently, the first tail 114 can be passed around downstream posts of the second set of posts 166, each downstream post being on a side opposite the previous post of the set. This, in turn, allows a second portion or tail 116 of the filament 112 to be advanced from the spool 113, through the filament management component 170, and wrapped around the first post 164f in the same manner as the first tail 114. Subsequent downstream movement of the second tail 116 tracks the same path that the first portion or tail 114 traveled. As the first and second tails 114, 116 progress downstream and wrap around the second and first sets of posts 166, 164, respectively, each time the tails 114, 116 intersect, the first tail 114 can pass over the second tail 116. Once the first tail 114 is wrapped around the last post 166t of the second set of posts 166, it can be passed through a thru-hole of the implant 180. The thru-hole can be the same or different from the thru-hole through which the first tail 114 passed after wrapping around the last post 164t.

The first tail 114 can then be passed in a direction B, back toward the filament management component 170, subsequently passed through the filament management component 170, and wrapped around a first post 168f of the third set of posts 168. As with the first two passes, the first tail 114 can be passed around downstream posts of the third set of posts 168 (e.g., last post 168t of the third set of post 168, and those posts of the third set preceding the last post 168t), each downstream post being on a side opposite the previous post of the set. This, in turn, allows the second tail 116 to be wrapped around the posts of the second set of posts 166, again tracking the same path that the first tail 114 traveled. Further, a third portion or tail 118 of the filament 112 can be advanced from the spool 113, through the filament management component 170, and be wrapped around the first set of posts 164, tracking the same path that the first tail 114 and then the second tail 116 traveled.

As the first, second, and third tails 114, 116, 118 progress downstream and wrap around the third, second, and first sets of posts 168, 166, 164, respectively, each time the tails 114, 116, 118 intersect, the third tail 118 can pass under the second tail 116 and over the first tail 114. The weaving pattern formed by the first, second and third tails 114, 116, 118 can result in the formation of a braided configuration 120. Meanwhile, as illustrated, as the first, second, and third tails 114, 116, 118 pass from the implant 180 and toward the filament management component 170, the tails 114, 116, 118 can have a generally straight configuration 130.

In embodiments having only three tails, after the first tail 114 has been wrapped around each of the three sets of posts 164, 166, 168, a leading end 114p of the first tail 114 can be secured to a portion of the filament 112 extending from the spool 113 and toward the sets of posts 160. The leading end 114p can be secured to any location proximate a trailing end 118t of the third tail 118 and a leading end 114t' of a second first tail 114' that extends from the spool 113. In the illustrated embodiment, the leading end 114p is secured to the later portion of the filament 112 at a location L.

By securing the leading end 114p to another portion of the filament 112, the path that defines the continuous braided closed loop 110 is set. More particularly, the path is defined by the posts of the first set 164 the first tail 114 is wrapped around, then the posts of the second set 166 the first tail 114 is wrapped around, and then the posts of the third set 168 that the first tail 114 is wrapped around. The second and third tails 116, 118 follow this path as well, as do second and subsequent first, second, and third tails that extend from the spool 113 and around the posts 160. The resulting configuration is what is illustrated in FIG. 3A, with the first tail 114 having passed around each of the three sets of the posts 164, 166, 168, the second tail 116 having passed around the first and second sets of posts 164, 166, and the third tail 118 having passed around the first set of posts 164. An approximate beginning and an approximate ending of each of the tails 114, 116, 118 is denoted by "x"s formed on the tails in the portion of the filament 112 having the substantially straight configuration 130. As the second first tail 114' begins to travel the path after the initial third tail 118, the initial first tail 114 will follow along with the second first tail 114'. The thickness of the loop 110 increases as additional tails are added from the spool 113. Once the desired thickness is achieved, the filament 112 can be cut from the spool 113, and the trailing end of the last tail can be secured to the loop 110.

Numerous filament fastening techniques known to those skilled in the art can be used to secure the leading end 114p to the filament 112 and to secure the trailing end of the last tail to the filament 112. These techniques include, but are not limited to using an adhesive, melting the two portions of filament together, and tying a knot. In one exemplary embodiment the leading end 114p and the trailing end of the last tail are secured to the filament using a hot melt adhesive.

Once the first tail 114 is manually braided with respect to the second and third tails 116, 118 and defines the path for the remaining portions of the filament 112 used to form the loop 110, subsequent advancement of the filament 112 can be automated, as described in greater detail below. The setting of the path allows the filament 112 to continue to follow the path as the filament progresses downstream through the posts 160 without having to manually weave the tails 114, 116, 118 with respect to each other. As the thickness of the loop 110 increases, the tails 114, 116, 118 continue to follow the defined path so that each subsequent tail added to the loop 110 becomes part of the continuous braided closed loop 110.

FIG. 3B schematically illustrates one exemplary embodiment of a system 200 for forming a continuous braided closed loop 210 using three filaments 214, 216, 218. The system 200 can generally include a plurality of pins or posts 260 disposed on a surface 254, a first filament 214, a second filament 216, and a third filament 218, with each filament being selectively passed around the posts 260 to form the continuous braided closed loop 210. As shown, the posts 260 can be divided into first, second, and third sets of posts 164, 166, 168, with adjacent posts in the same set being opposite and staggered from one another. Similar to FIG. 3A, the posts 260 of FIG. 3B are schematically represented by rectangles, and thus the illustrated embodiment is not necessarily representative of how filaments 214, 216, 218 pass around the posts 260.

Also similar to FIG. 3A, each set of posts 264, 266, 268 can be visually distinguishable from each other, and each of the first, second, and third filaments 214, 216, 218 can also be visually distinguishable from each other. Accordingly, in one exemplary embodiment, the first set of posts 264 can be predominantly blue, the second set of posts 266 can be predominantly red, and the third set of posts 268 can be predominantly green, while the first filament 214 can be predominantly blue, the second filament 216 can be predominantly red, and the third filament 218 can be predominantly green. Such an embodiment can assist a user in knowing which filaments should be associated with which posts. In other embodiments, it may be desirable for the continuous braided closed loop 210 to have the same color throughout, and thus each filament 214, 216, 218 may have the same color and no other visually distinguishing characteristics associated therewith. A person skilled in the art will recognize other visual and tactile characteristics that can be associated with the posts and/or filaments to assist a user in distinguishing portions of the system, including but not limited to each filament having a different texture or size.

Each of the first, second, and third filaments can be stored or located using any number of components known to those skilled in the art for holding a filament before having that filament introduced to the pins or posts. In one exemplary embodiment, each is located on respective spools 213, 215, 217 prior to being introduced to the posts 260. The system 200 can also include an implant 280 and a filament management component 270, similar to like components 180, 170 in the system 100.

In use, the first filament 214 can be advanced from the spool 213, through the filament management component 270, and to a first post 264$f$ of the first set of posts 264. The first filament 214 can be wrapped around at least a portion of the post 264$f$, which as discussed above can include passing it around an outside portion of the post 264$f$. The filament 214 can then be passed around downstream posts of the first set of posts 264, with each downstream post being on a side opposite the previous post of the set. Once the first filament 214 is wrapped around a last post 264$t$ of the first set of posts 264, it can be passed through a thru-hole of the implant 280 and then passed in a direction A, back toward the filament management component 270. Unlike the system of FIG. 3A, however, the first filament 214 does not then extend to the second or third set of posts 266, 268. Rather, a leading end 214$p$ of the first filament 214 is secured to a portion of the first filament 214 extending from the spool 213 and toward the first set of posts 264 at an approximate location L' using techniques described herein or otherwise known to those skilled in the art.

For reference purposes, the portion of the first filament 214 extending between the leading end 214$p$ and the location just proximate to the location L' can be described as a first tail 214$t_1$ of the first filament 214. By securing the leading end 214$p$ to a later portion of the first filament 214, the path of the first filament 214 is set to only pass around the first set of posts 264. As a second tail 214$t_2$ of the first filament 214 is passed toward the posts 264, the second tail 214$t_2$ being just distal of the location L', the first tail 214$t_1$ follows along and a thickness of a loop 210$t_1$ formed by the first filament 214 increases. Each subsequent pass around the posts 264 adds an additional tail to the loop 210$t_1$. Once the desired thickness of the first loop 210$t_1$ is achieved, the first filament 214 can be cut, and the trailing end of the last tail can be secured to the loop 210$t_1$ using techniques consistent with those described herein.

The second and third filaments 216, 218 can be advanced from their respective spools 215, 217, through the filament management component 270, and to a first post 266$f$, 268$f$ of the respective second and third sets of posts 266, 268 in a similar manner as the first filament 214. The second and third filaments 216, 218 can be wrapped around at least a portion of their respective first posts 266$f$, 268$f$, and subsequently passed around downstream posts of the second and third sets of posts 266, 268, with each downstream post being on a side opposite the previous post of the set. As the second filament 216 progresses downstream and wraps around the second set of posts 266, each time the second filament 216 intersects the first filament 214, the second filament 216 can pass under the first filament 214. Further, as the third filament 218 progresses downstream and wraps around the third set of posts 268, each time the third filament 218 intersects the second filament 216, it can pass under the second filament 216, and each time the third filament 218 intersects the first filament 214, it can pass over the first filament 214. This weaving of the first, second, and third filaments 214, 216, 218 can result in a braided configuration 220. As the first, second, and third filaments 214, 216, 218 pass from the implant 280 and toward the filament management component 270, the filaments 214, 216, 218 can have a generally straight configuration 230.

Once the second and third filaments 216, 218 are wrapped around the last posts 266$t$, 268$t$ of the respective second and third sets of posts 266, 268, they can be passed through one or more thru-holes of the implant 280 and then passed in directions B and C, respectively, back toward the filament management component 270. A leading end 216$p$ of the second filament 216 can then be secured to a portion of the second filament 216 extending from the spool 215 and toward the second set of posts 266 at an approximate location M' using techniques described herein or otherwise known to those skilled in the art. Likewise, a leading end 218$p$ of the third filament 218 can then be secured to a portion of the third filament 218 extending from the spool 217 and toward the third set of posts 268 at an approximate location N' using techniques described herein.

Accordingly, similar to the first filament 214, paths for the second and third filaments 216, 218 are set by securing their leading ends 216$p$, 218$p$ to later portions of the respective filaments 216, 218. For reference purposes, the portion of the second filament 216 extending between the leading end 216$p$ and the location just proximate to the location M' can be described as a first tail 216$t_1$ of the second filament 216, and the portion of the third filament 218 extending between the leading end 218$p$ and the location just proximate to the location N' can be described as a first tail 218$t_1$ of the third filament 218. Each subsequent pass around the second and third sets of posts 266, 268 adds an additional tail, e.g., 216$t_2$, 218$t_2$, to loops 210$t_2$, 210$t_3$ formed by the second and third filaments 216, 218, respectively, thereby increasing a thickness of each loop 210$t_2$, 210$t_3$. Once the desired thicknesses of the second and third loops 210$t_2$, 210$t_3$ are achieved, the respective second and third filaments 216, 218 can be cut, and trailing ends of their respective last tails can be secured to the respective loops $210t_2$, $210t_3$ using techniques consistent with those described herein.

Downstream movement of the first, second, and third filaments 214, 216, 218, can occur in any desired order. For example, in some embodiments each filament may progress downstream at a similar rate and at a similar time. Alternatively, in other embodiments a desired thickness of the first loop $210t_1$ may be achieved before forming the second or third loops $210t_2$, $210t_3$, and then a desired thickness of a second loop $210t_2$ may be achieved before forming the third loop $210t_3$. Any other order or progression of the filaments 214, 216, 218 around the posts 264, 266, 268 can be used without departing from the spirit of the present disclosure.

While in the system of FIG. 3B, three separate loops $210t_1$, $210t_2$, $210t_3$ are formed, the braided configuration 220 created during the first pass of the first, second, and third filaments 214, 216, 218 through the posts 260 allows the three separate loops $210t_1$, $210t_2$, $210t_3$ to be braided together to form a single continuous braided closed loop 210. Thus, similar to the system of FIG. 3A, the path of the single continuous braided closed 210 is set manually during the first pass of each filament 214, 216, 218, and thus subsequent advancement of the first, second, and third filaments 214, 216, 218 can be automated. The setting of the three individual paths, and then combining them to form a single path for the continuous loop 210 allows the filaments 214, 216, 218 to follow their individual paths while combining to form the continuous loop 210. As the thickness of each individual loop $210t_1$, $210t_2$, $210t_3$ increases, the filaments 214, 216, 218 continue to follow the paths so that each subsequent tail of each filament 214, 216, 218 added to each individual loop $210t_1$, $210t_2$, $210t_3$ becomes part of the continuous braided closed loop 210.

The continuous braided closed loops 110, 210 that result from the schematic configurations of FIGS. 3A and 3B can include substantial lengths that have the braided configuration 120, 220 and substantial lengths that have the generally straight configuration 130, 230. This is because the portions of filament that pass around the posts have the braided configuration, but the portions of filament that pass from the downstream end and toward the upstream end have the generally straight configuration. Thus, roughly only half or less of the circumference of the resulting loop has a braided configuration, while the rest has a generally straight configuration.

Figure 4A:
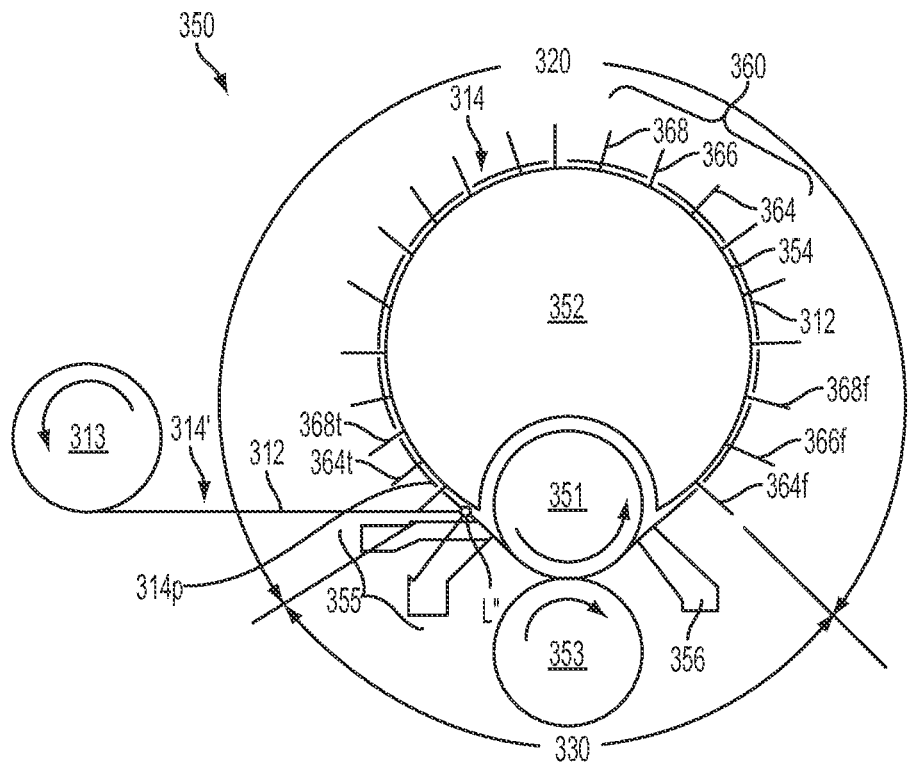
FIG. 4A is a side view of one exemplary embodiment of a system for use in manufacturing a continuous braided closed loop implant.
Figure 4B:
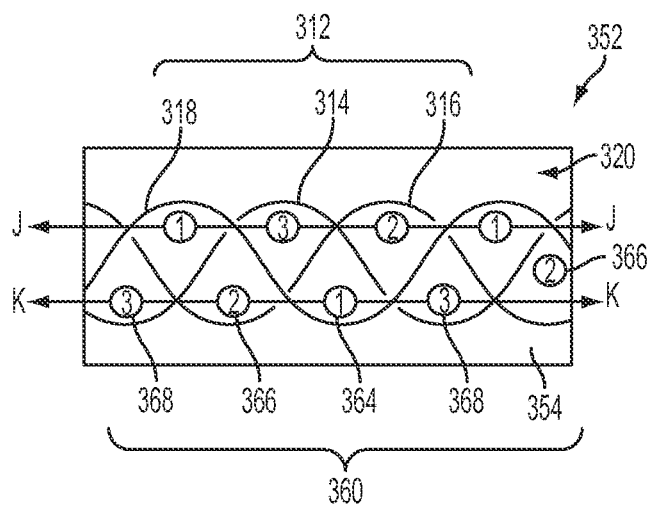
FIG. 4B is a flattened, top view of a mandrel of the system of FIG. 4A.

FIGS. 4A and 4B illustrate one exemplary embodiment of a machine 350 for use in forming a continuous braided closed loop. The machine 350 can include a mandrel 352 having a plurality of posts 360 disposed on a surface 354 thereof and mechanical components to assist in advancing filament 312 around the mandrel 352, particularly after a path for the filament 312 has been set. These mechanical components can include a grip roller 351, a pinch roller 353, and one or more fiber guides 355, 356. One or more spools of filament can be provided for use with the machine 350. In the illustrated embodiment, one spool 313 of filament 312 is provided, and thus the filament 312 can be divided into multiple tails and associated with respect to the posts 360 in a manner similar to as described with respect to the system 100 of FIG. 3A. In other embodiments, a plurality of spools, for instance three spools, can be provided, with each spool having a different filament. In such embodiments, each spool can be used as its own tail and can be associated with respect to the posts 360 in a manner similar to as described with respect to the system 200 of FIG. 3B.

Similar to the schematic illustrations of FIGS. 3A and 3B, and as illustrated in FIG. 4B, the posts 360 of the mandrel 352 can be divided into three or more sets of posts 364, 366, 368, with each downstream post of a set being staggered and opposite from the previous post of the set. In some embodiments some or all of the posts 360 can be configured to rotate 360 degrees relative to the mandrel 352 to further assist in advancing the filament 312 around the mandrel 352. Additionally, similar to the schematic systems of FIGS. 3A and 3B, the posts 360 can have visual, tactile, or other distinguishing features to help a user know which individual posts are with which set of posts. Still further, in some embodiments the posts 360 can be retractable such that they can be selectively partially or fully disposed within the mandrel 352. This can be useful, for example, once the continuous braided closed loop is fully formed and is ready to be removed from the machine 350. Retracting the posts 360 can make it easy to access the loop without struggling to pull it off any of the posts 360.

As shown, the grip and pinch rollers 351, 353 can be disposed near a bottom portion of the mandrel 352 and can be configured to receive filament 312 as it extends from the spool 313 on which it is stored. In one embodiment the spool 313 can rotate in a counter-clockwise direction to advance the filament 312 toward the grip and pinch rollers 351, 353. The grip and pinch rollers 351, 353 can rotate in opposite direction to tension the filament 312 and advance it toward the posts 360 of the mandrel 352. In the illustrated embodiment the grip roller 351 rotates in a counter-clockwise direction and the pinch roller 353 rotates in a clockwise direction. In exemplary embodiments, the mandrel 352 remains substantially stationary, i.e., it does not rotate, during the formation of a continuous braided closed loop.

The fiber guides 355, 356 can help direct the filament 312 towards the posts 360 on the mandrel 352. In some embodiments the fiber guides 355, 356 can be stationary such that they generally engage filament 312 passing thereby, while in other embodiments the guides 355, 356 can move between a position that does not engage the filament 312 and a position that engages the filament 312. The fiber guides 355, 356 can help guide and tension the filament 312 by engaging it. A person skilled in the art will recognize other components that can be used to help guide filament. Additionally, in some embodiments the machine 350 can be configured such that the filament 312 is already directed toward the posts 360 and thus no additional guides are needed to assist in directing the filament 312.

A size and shape of the continuous braided closed loop formed by the machine 350 can depend, at least in part, on a size of the mandrel 352. In turn, the size and shape of the mandrel 352 can depend, at least in part, on the other components with which the mandrel will be used, the desired configuration of the loop, and the type of procedure in which the loop will be used. In one exemplary embodiment the mandrel 352 is substantially circular in shape and has a diameter in the range of about 10 millimeters to about 100 millimeters, and in one embodiment it has a diameter of about 30 millimeters.

Each post 360 on the mandrel 352 can have a variety of shapes and sizes. In the illustrated embodiment, each post 360 has substantially the same shape and dimensions, although they do not necessarily have to be the same shapes or dimensions. In one exemplary embodiment each post 360 is substantially cylindrical in shape, has a diameter in the range of about 0.5 millimeters to about 1.5 millimeters, and has a length in the range of about 5 millimeters to about 10 millimeters. In one embodiment each post 360 has a diameter of about 0.8 millimeters and a length of about 6 millimeters.

The sizes and shapes of the posts 360, as well as the number of posts per set and the number of sets of posts, can have an impact on the braided configuration that results from disposing filament around the posts. While any number of posts can be used, in one exemplary embodiment the number of posts disposed on the mandrel can be in the range of approximately 10 posts to approximately 28 posts, and one embodiment there can be approximately 16 posts disposed on the mandrel. Likewise, while any number of post sets can be used, in one exemplary embodiment the number of sets of posts can be in the range of about 3 sets to about 12 sets, and more specifically can be in the range of about 3 sets to about 6 sets. The number of posts sets can define the number of tails, or the number of filaments used when multiple filaments are used to form the continuous braided closed loop.

The configurations of the posts 360 with respect to each other can also impact the resulting braided configuration of the loop. Thus, while in the illustrated embodiment adjacent posts 360 are opposite and staggered form one another, with a spacing between the posts being substantially similar and the posts generally forming two straight lines J and K, a person skilled in the art will recognize a variety of other configurations that can be formed by the posts 360 by disposing the posts in different locations on the mandrel 352 than illustrated.

Sizes and shapes of the spool 313, grip roller 351, pinch roller 353, and fiber guides 355, 356 generally have a less significant impact on the size and shape of the loop that is formed. As shown, each of the spool 313, grip roller 351, and pinch roller 353 are substantially circular in shape, and the fiber guides 355, 356 are substantially polygonal and elongate in shape. Exemplary diameters of the grip and pinch rollers 351, 353 can be in the range of about 5 millimeters to about 50 millimeters, and in one embodiment they can have diameters of about 10 millimeters. An exemplary diameter of the spool 313 can be in the range of about 30 millimeters to about 100 millimeters, and in one embodiment it has a diameter of about 60 millimeters. The size of the fiber guides 355, 356 can be selected by a person having skill in the art in view of the sizes of the other components of the machine 350 and system, and the type and size of the filament 312 used to form the loop.

In use, a strand of suture filament 312 can be passed form the spool 313 and advanced toward the mandrel 352 for disposal around the posts 360 in a manner similar to as described with respect to the systems of FIGS. 3A and 3B. The filament 312, or more particularly a first tail 314 (FIG. 4B), can be brought past the first fiber guide 355, through the grip and pinch rollers 351, 353, and past the second fiber guide 356, toward a first post 364f of the first set of posts 364. The first tail 314 can then be selectively wrapped around the downstream posts of the first set of posts 364 in a manner similar to as described for the schematic systems 100, 200. After the first tail 314 wraps around a last post 364t of the first set of posts 364, the filament 312 can again go past the first fiber guide 355, through the grip and pinch rollers 351, 353, and past the second fiber guide 356, toward a first post 366f of the second set of posts 366.

The first tail 314 can then be selectively wrapped around the downstream posts of the second set of posts 366, past the first fiber guide 355, through the grip and pinch rollers 351, 353, and past the second fiber guide 356, toward a first post 368f of the third set of posts 368. As a result, a second tail 316 (FIG. 4B) of the filament 312 that follows the first tail 314 can follow the path of the first tail 314 around the first set of posts 364. Each time the first and second tails 314, 316 intersect, the first tail 314 can pass over the second tail 316.

The first tail 314 can then be wrapped around the third set of posts 368, which in turn means the second tail 316 wraps around the second set of posts 366 and a third tail 318 (FIG. 4B) wraps around the first set of posts 364. As the third tail 318 intersects the first and second tails 314, 316, it can be passed under the second tail 316 but over the first tail 314 such that the weave of the three tails 314, 316, 318 forms a braided configuration 320. This configuration is illustrated more clearly in FIG. 4B, and is more readily understood in view of the descriptions associated with the systems 100, 200 of FIGS. 3A and 3B.

After the first tail 314 wraps around a last post 368t of the third set of posts 368, a leading end 314p of the first tail 314 can be secured to a portion of the filament 312 about to move toward the grip and pinch rollers 351, 353 for the first time, i.e., a second first tail 314' or a terminal end of the third tail, to set the path for the continuous braided closed loop. In the illustrated embodiment the first tail is coupled to the filament 312 at a location L". Securing the leading end 314p to the filament 312 at the location L" can be done in any manner consistent with the present disclosure.

In one exemplary embodiment, the initial path set by the first tail 314 prior to securing it to the filament 312 at the location L" can be done manually, with a user weaving the first, second, and third tails 314, 316, 318 into the braided configuration 320 around a circumference of the mandrel 352. Once the leading end 314p of the first tail 314 is secured to a later portion of the filament 312, however, mechanical components, such as the rollers 351, 353, guides 355, 356, and rotation of the posts 360, can be operated to automate subsequent passes of filament 312 around the mandrel 352. The filament 312 can then continue to be run through the machine 350, following the path set by the first tail 314, until a desired thickness is achieved. Once the loop is complete, a trailing end of the last tail can be secured to the loop in any manner consistent with the present disclosure. The loop can then be removed from the machine 350 for subsequent use as an implant. In some embodiments the loop can be worked off the posts 360 by hand, while in other embodiments the posts 360 can be retracted at least partially into the mandrel 352 to allow the loop to be easily removed.

While the loops 110, 210 formed using the systems 100, 200 in FIGS. 3A and 3B include braided and straight configurations 120, 130 and 220, 230 each of a substantial length, the continuous braided closed loop that results from using the machine 350 of FIGS. 4A and 4B is one in which the braided configuration 320 is a substantial majority of the circumference of the loop. As shown, the braided configuration 320 is the portion disposed around the posts 360 of the mandrel 352 while a generally straight configuration 330 is only the portion between the first and last pins 360 of the mandrel 352.

A continuous braided closed loop 310 formed in the manner described herein can be associated with one or more implants for use in surgical procedures. FIGS. 5A-5B and 6A-6B illustrate two such embodiments. In FIGS. 5A and 5B, the loop 310 is attached to a cortical button 308. A person skilled in the art will recognize any number of configurations an implant such as a cortical button can have, but in the illustrated embodiment the button 306 has a body 308 having a length l and a width w with two outer thru-holes 307o and two inner thru-holes 307i formed therethrough. The loop 310 can be disposed through any number of the thru-holes 307i, 307o, but as shown it is disposed through the two inner thru-holes 307i. Although in the illustrated embodiment diameters of the inner thru-holes 307i are larger than thickness of the loop 310, in other embodiments the thru-hole 307i, 307o diameters can be approximately the same as the thickness of the loop 310 to form a reasonably secure fit between the loop 310 and the implant.

In exemplary embodiments the body 308 is made from a stainless steel or titanium, but any number of polymers, metals, or other biocompatible materials in general can be used to form the body. Some non-limiting examples of biocompatible materials suitable for forming the body include a polyether ether ketone (PEEK), bioabsorbable elastomers, copolymers such as polylactic acid-polyglycolic acid (PLA-PGA), and bioabsorbable polymers such as polylactic acid. The implant can also be formed of absorbable and non-absorbable materials. Other exemplary embodiments of a cortical button or similar implant that can be used in conjunction with the teachings herein are described at least in U.S. Pat. No. 5,306, 301 of Graf et al., the content of which is incorporated by reference herein in its entirety.

In FIGS. 6A and 6B, the loop 310 is attached to a suture anchor 306'. A person skilled in the art will recognize any number of configurations an implant such as a suture anchor can have, but in the illustrated embodiment the anchor 306' has a body 308' having a length l' and a width w' with two thru-holes 307' formed therethrough, and threads 305' formed on an outer surface of the anchor 306' and adapted for insertion into bone. As shown the loop 310 is disposed through each of the thru-holes 307'. Exemplary embodiments of suture anchors for use with the continuous braided closed loop include a Gryphon™ anchor that is commercially available from DePuy Mitek, LLC.

Figure 7A:
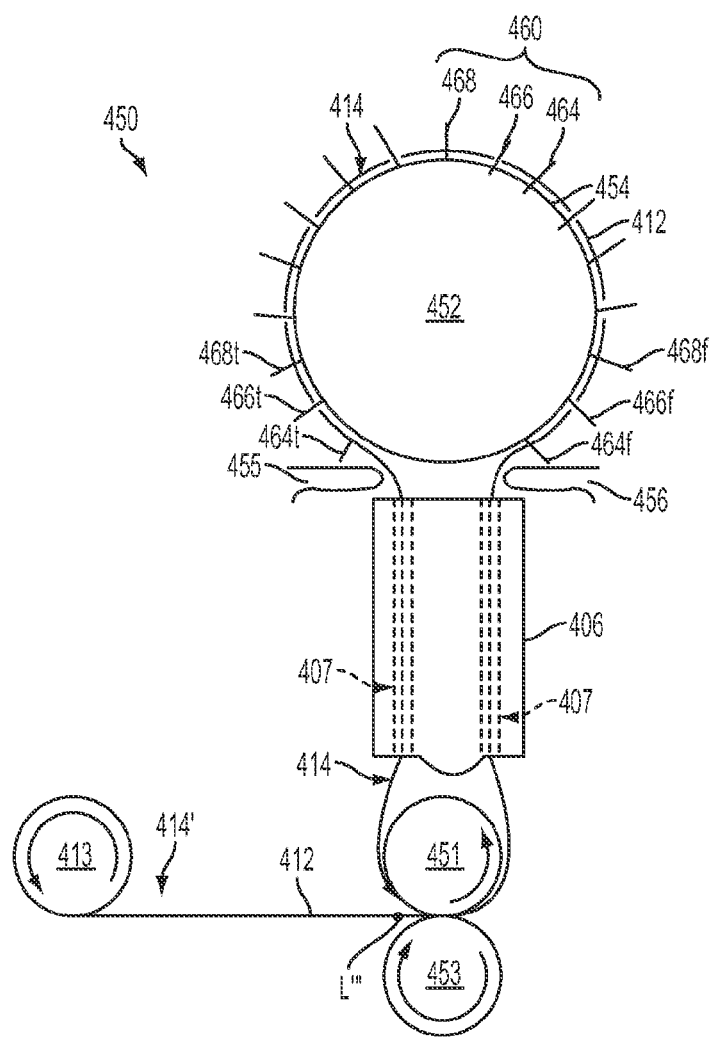
FIG. 7A is a side view of one exemplary embodiment of a system for use in manufacturing a continuous braided closed loop attached to an implant.
Figure 7B:
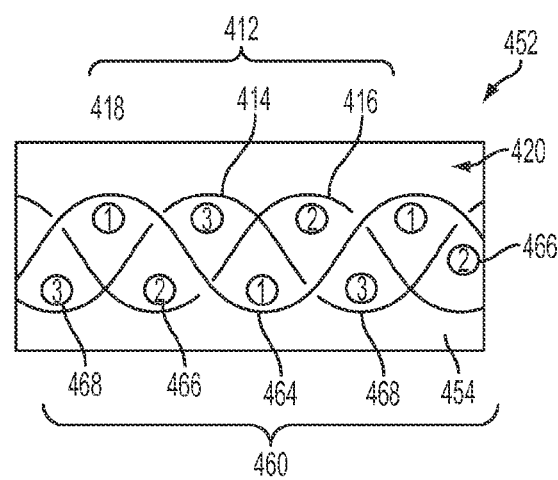
FIG. 7B is a flattened, top view of a mandrel of the system of FIG. 7A.

FIGS. 7A and 7B illustrate an alternative set-up of a machine 450 for use in forming a continuous braided closed loop. The machine 450 is similar to the machine 350 of FIGS. 4A and 4B, as the mandrel 452, the mandrel's surface 454, posts 460, grip roller 451, pinch roller 453, fiber guides 455, 456, and spool 413 of filament 412 can be similarly configured. The difference is that disposed between the mandrel 452 and the rollers 451, 453 is an implant, as shown a suture anchor 406. Thus as the filament 412 passes from the rollers 451, 453 and toward a first post 464f, 466f, 468f of any of the first, second, and third sets of posts 464, 466, 468, the filament 412 first passes through a thru-hole 407 of the anchor 406 and then past the second fiber guide 456 before engaging the posts 460. Likewise, after the filament 412 passes the last pin 464t, 466t, 468t of the first, second, and third sets of posts 464, 466, 468, the filament 412 moves past the first fiber guide 455 and through a thru-hole 407 of the anchor 406 before passing again through the rollers 451, 453.

In the illustrated embodiment, after a first tail 414 (FIG. 7B) sets the path by going through each set of posts 464, 466, 468, and is manipulated with respect to a second tail 416 (FIG. 7B) and a third tail 418 (FIG. 7B) to form a braided configuration 420, the first tail 414 can be coupled to the filament 412 at a location L''', which is distal of the anchor 406. The location L''' can be proximate to a beginning of the second first tail 414' and/or the terminal end of the third tail 418, and further, can be located before that portion of the filament 412 passes between the grip and pinch rollers 451, 453. The braided configuration 420 formed by the tails 414, 416, 418 of the filament 412 is illustrated more clearly in FIG. 7B, and is more readily understood in view of the descriptions associated with the systems 100, 200 of FIGS. 3A and 3B. Similar to previous embodiments, FIG. 7B illustrates one of many possible configurations of the first, second, and third posts 464, 466, 468 on the surface 454 of the mandrel 452.

FIGS. 8A-8B and 9A-9B illustrate two exemplary post configurations that differ from previous embodiments, and thus create different braided configurations for the loop. A person skilled in the art will recognize that these two configurations in no way limit the number of possible braided configurations that can be formed in loops without departing from the spirit of the present disclosure.

Figure 8A:
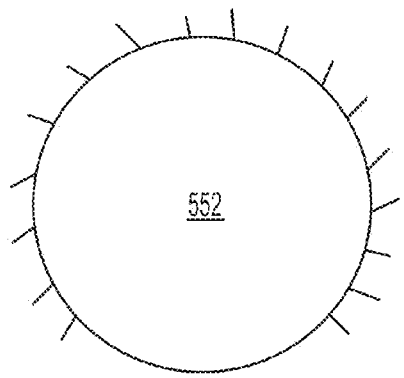
FIG. 8A is a side view of one exemplary embodiment of a mandrel for use in a system for manufacturing two continuous braided closed loops.
Figure 8B:
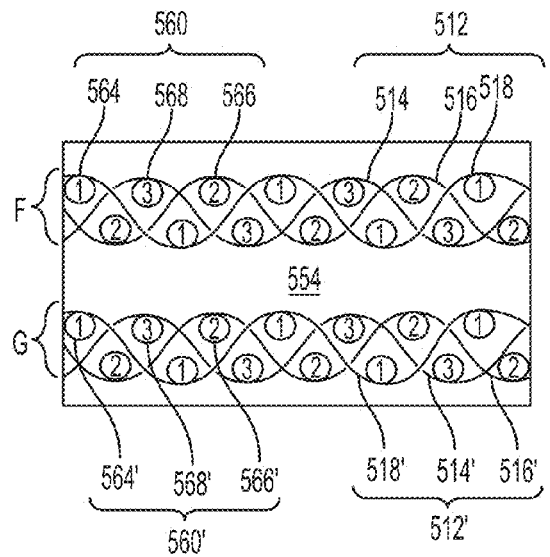
FIG. 8B is a flattened, top view of the mandrel of FIG. 8A.

FIGS. 8A and 8B illustrate a mandrel 552 having two distinct rows F, G of posts 560. 560'. A first row F includes a first set of posts 564, a second set of posts 566, and a third set of posts 568 formed on a surface 554 of the mandrel 552. Likewise, a second row G also formed on the surface 554 includes a first set of posts 564', a second set of posts 566', and a third set of posts 568'. As shown in FIG. 8B, the configurations of each row F, G can be substantially similar, meaning that continuous braided closed loop that is formed on the first row F can be substantially similar to the continuous braided closed loop that is formed on the second row G.

A single filament, or a plurality of filaments, can be wrapped around each of the rows F, G in manners consistent with the present disclosure. Accordingly, as shown in FIG. 8B, a first tail 514 of the first filament 512 can be disposed around the third set of posts 568 after having initially been disposed around the first and second sets of posts 564, 566, a second tail 516 of the first filament 512 can be disposed around the second set of posts 566 after having initially been disposed around the first set of posts 564, and a third tail 518 of the first filament 512 can be disposed around the first set of posts 564. Likewise, a first tail 514' of a second filament 512' can be disposed around the third set of posts 568' after having been disposed around the first and second sets of posts 564', 566', a second tail 516' of the second filament 512' can be disposed around the second set of posts 566' after having initially been disposed around the first set of posts 564', and a third tail 518' of the second filament 512' can be disposed around the first set of posts 564'. Consistent with the present disclosures, these configurations result from the paths set by the first tails 514, 514'. Further, the first, second, and third tails 514, 516, and 518 of the first filament 512 can be woven together to form a braided configuration, and the first, second, and third tails 514', 516', 518' of the second filament 512' can be woven together to form a braided configuration, in manners consistent with the present disclosure.

The mandrel 552 can be associated with other components of a system, including grip and pinch rollers, fiber guides, spools, and implants, and be operated in a similar manner as described herein. The mandrel 552 of FIGS. 8A and 8B allows two loops to be formed at once, and if an implant, such as a cortical button or anchor, is directly associated with the machine, such as in FIG. 7A, then the two loops can be attached directly to the implant. Depending on the number of thru-holes formed in the implant, and the desired configuration, the loops can be disposed in the same or different thru-holes of the implant. Implants having two similarly-sized continuous braided closed loops attached thereto can be useful, for example, in providing additional strength to hold tissue at a desired location with respect to bone.

Figure 9A:
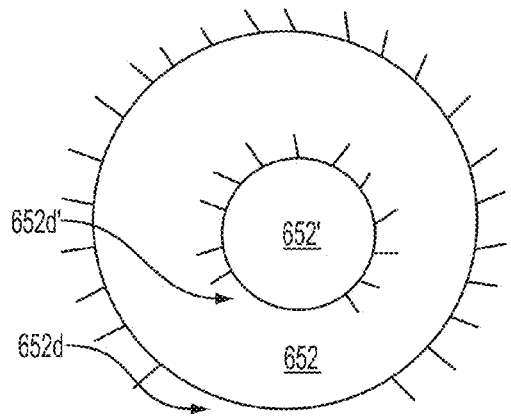
FIG. 9A is a side view of one exemplary embodiment of two mandrels for use in a system for manufacturing two continuous braided closed loops.
Figure 9B:
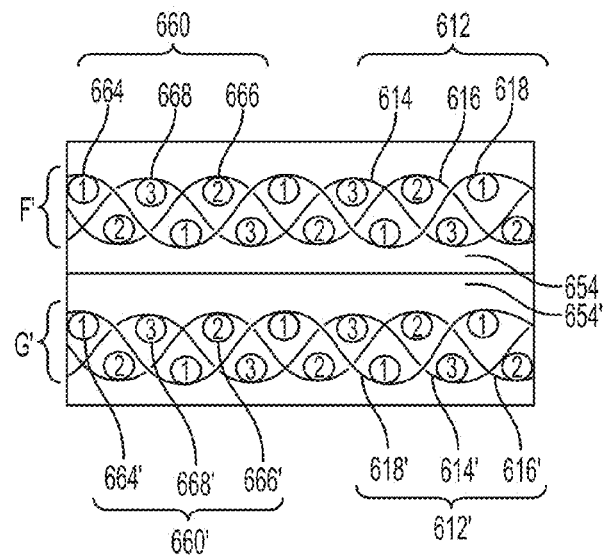
FIG. 9B is a flattened, top view of the two mandrels of FIG. 9A.

FIGS. 9A and 9B illustrate two distinct mandrels 652, 652', with each mandrel having a row F', G' of posts 660, 660' formed thereon. The first row F' formed on the mandrel 652 can include a first set of posts 664, a second set of posts 666, and a third set of posts 668 formed on a surface 654 thereof. Likewise, the second row G' formed on the mandrel 652' can include a first set of posts 664', a second set of posts 666', and a third set of posts 668' formed on a surface 654' thereof. As shown, the first mandrel 652 is larger than the second mandrel 652'. As a result, a continuous braided closed loop that is formed on the first mandrel 652 can have a larger diameter than a continuous braided closed loop that is formed on the second mandrel 652'. Although in the illustrated embodiment the mandrels 652, 652' are approximately concentric, they do not have to be. For example, in some embodiments distal ends 652d, 652d' of the respective mandrels 652, 652' can be substantially aligned.

A single filament, or a plurality of filaments, can be wrapped around each of the rows F', G' in manners consistent with the present disclosure. Accordingly, as shown in FIG. 9B, a first tail 614 of the first filament 612 can be disposed around the third set of posts 668 after having initially been disposed around the first and second sets of posts 664, 666, a second tail 616 of the first filament 612 can be disposed around the second set of posts 666 after having initially been disposed around the first set of posts 664, and a third tail 618 of the first filament 612 can be disposed around the first set of posts 664. Likewise, a first tail 614' of a second filament 612' can be disposed around the third set of posts 668' after having been disposed around the first and second sets of posts 664', 666', a second tail 616' of the second filament 612' can be disposed around the second set of posts 666' after having initially been disposed around the first set of posts 664', and a third tail 618' of the second filament 612' can be disposed around the first set of posts 664'. Consistent with the present disclosures, these configurations result from the paths set by the first tails 614, 614'. Further, the first, second, and third tails 614, 616, and 618 of the first filament 612 can be woven together to form a braided configuration, and the first, second, and third tails 614', 616', 618' of the second filament 612' can be woven together to form a braided configuration, in manners consistent with the present disclosure.

In view of the disclosures herein, a person having skill in the art will understand how the two mandrels 652, 652' can be associated with other components of a system, such as grip and pinch rollers, fiber guides, spools, and implants, and be operated in a manner consistent with the present disclosures. In embodiments in which an implant is directly associated with the machine, such as in FIG. 7A, the two loops can be attached directly to the implant using any number of thru-holes formed therein.

Figure 10A:
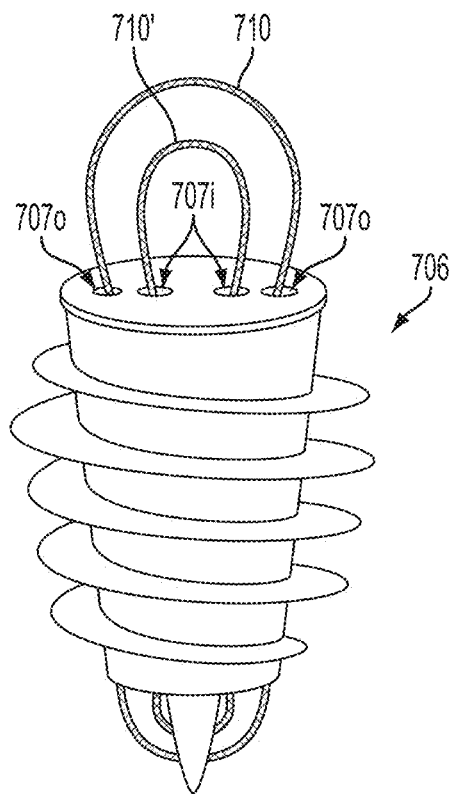
FIG. 10A is a perspective view of one exemplary embodiment of a surgical construct having two continuous braided closed loops attached to an implant.
Figure 10B:
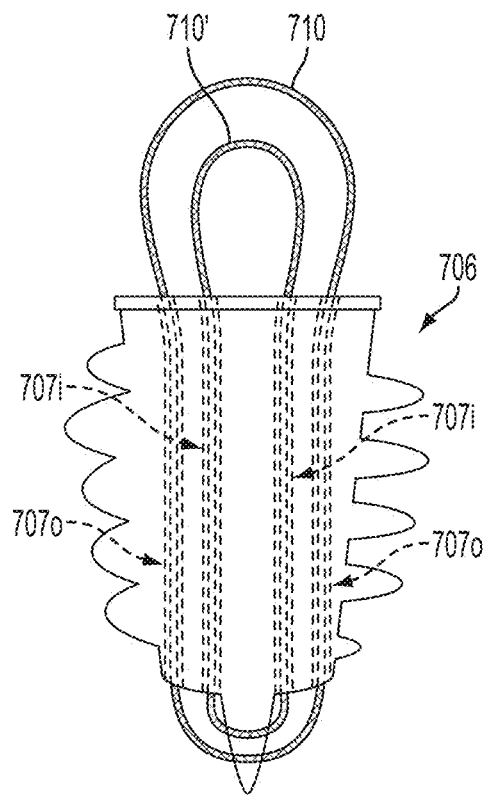
FIG. 10B is a side view of the surgical construct of FIG. 10A.

FIGS. 10A and 10B illustrate one exemplary embodiment of a suture anchor 706 having different sized loops 710, 710' attached thereto. As shown, the first, larger loop 710 can be disposed through outer thru-holes 707o and the second, smaller loop 710' can be disposed through inner thru-holes 707i. The other features of the loops 710, 710' and anchor 706 can be consistent with the disclosures contained herein and the knowledge of those skilled in the art. Implants having two differently-sized continuous braided closed loops attached thereto can be useful, for example, to hold the same piece of tissue at separate locations, or to hold two separate tissues at desired locations with respect to the same bone.

One skilled in the art will appreciate further features and advantages of the invention based on the above-described embodiments. Accordingly, the invention is not to be limited by what has been particularly shown and described, except as indicated by the appended claims. By way of non-limiting example, a person skilled in the art will recognize other ways braided configurations can be formed in view of the disclosures herein, and thus to the extent a braided configuration is described in a particular manner, in no way are braided configurations limited to formation in that particular manner. All publications and references cited herein are expressly incorporated herein by reference in their entirety.

What is claimed is:

1. An implantable surgical construct, comprising:
    an implant having a body with a first thru-hole formed therein; and
    a continuous braided closed filament loop having an attachment portion attached to the implant through the first thru-hole and a free portion that extends from the implant, the closed filament loop configured to be formed from a single strand of filament having at least three tails such that a second tail is passed under a first tail a plurality of times and a third tail is passed between the first tail and the second tail a plurality of times.

2. The construct of claim 1, wherein the implant comprises a suture anchor.

3. The construct of claim 1, wherein the implant has a length greater than a width.

4. The construct of claim 1, wherein the implant includes a second thru-hole formed therein and spaced a distance apart from the first thru-hole.

5. The construct of claim 1, wherein the closed filament loop comprises a plurality of closed filament loops, each loop being formed from a single braided strand of filament having at least three tails.

6. The construct of claim 1, further comprising at least one additional continuous braided closed filament loop having an attachment portion attached to the implant through a second thru-hole and a free portion that extends from the implant, the additional closed filament loop configured to be formed from a single strand of filament having at least three tails such that a second tail is passed under a first tail a plurality of times and a third tail is passed between the first tail and the second tail a plurality of times.

7. The construct of claim 6, wherein the first continuous braided closed filament loop and the at least one additional continuous braided closed filament loop have approximately the same loop diameter.

8. The construct of claim 6, wherein the single filament of the first continuous braided closed filament loop and the single filament of the at least one additional continuous braided closed filament loop are visually distinct.

9. The construct of claim 1, wherein at least one-quarter of the circumference of the continuous braided closed filament loop has a continuous braided configuration formed by the first, second, and third tails, and wherein at least one-quarter of the circumference of the continuous braided closed filament loop has a straight configuration in which the first, second, and third tails extend a continuous length without being braided together.

10. A method of manufacturing an implantable surgical connector loop, comprising:
    passing a first tail of a single strand of filament around a first set of posts on a mandrel, the posts of the first set of posts being arranged in a pattern such that adjacent posts are opposite and staggered from one another and the filament changing direction as it passes around each post in the first set of posts;
    passing the first tail around a second set of posts on the mandrel, the posts of the second set of posts being arranged in a pattern such that adjacent posts are opposite and staggered from one another and the filament changing direction as it passes around each post in the second set of posts, wherein a second tail of the single strand of filament then passes around the first set of posts on the mandrel and is disposed under the first tail when the first and second tails intersect; and
    passing the first tail around a third set of posts on the mandrel, the posts of the third set of posts being arranged in a pattern such that adjacent posts are opposite and staggered from one another and the filament changing direction as it passes around each post in the third set of posts, wherein the second tail then passes around the second set of posts on the mandrel and a third tail of the single strand of filament then passes around the first set of posts on the mandrel and is woven between the first and second tails in an alternating over-under pattern to form a braid, and a leading terminal end of the first tail is fixedly secured to a portion of the single strand of filament before it is passed around the first set of posts a first time such that a continuous braided closed loop is formed, wherein the first tail of the single strand of filament is passed through at least one thru-hole formed in a surgical implant when moving from the first set of posts to the second set of posts and when moving from the second set of posts to the third set of posts such that the continuous braided closed loop is coupled to the surgical implant.

11. The method of claim 10, further comprising actuating mechanical components associated with the mandrel to automatically repeat the steps of passing the first tail around the first, second, and third sets of posts to increase a thickness of the continuous braided closed loop.

12. The method of claim 11, wherein operating mechanical components associated with the mandrel comprises rotating at least one roller to slidably move the single strand of filament relative to the first, second, and third sets of posts.

13. The method of claim 11, wherein operating mechanical components associated with the mandrel comprises rotating the first, second, and third sets of posts to help move the single strand of filament relative to the implant.

14. A method of manufacturing a surgical implant, comprising:
  passing a first strand of filament around a first set of posts on a mandrel, the posts of the first set of posts being arranged in a pattern such that adjacent posts are opposite and staggered from one another and the first strand of filament changing direction as it passes around each post in the first set of posts, and fixedly securing a leading end of the first strand of filament to a mid-portion of the first strand of filament to form a first closed loop disposed around the mandrel;
  passing a second strand of filament around a second set of posts on the mandrel, the posts of the second set of posts being arranged in a pattern such that adjacent posts are opposite and staggered from one another and the second strand of filament changing direction as it passes around each post in the second set of posts, fixedly securing a leading end of the second strand of filament to a mid-portion of the second strand of filament to form a second closed loop disposed around the mandrel, and the second strand of filament being disposed over the first strand of filament when the first and second strands intersect;
  passing a third strand of filament around a third set of posts on the mandrel, the posts of the third set of posts being arranged in a pattern such that adjacent posts are opposite and staggered from one another and the third strand of filament changing direction as it passes around each post in the third set of posts, fixedly securing a leading end of the third strand of filament to a mid-portion of the third strand of filament to form a third closed loop disposed around the mandrel, and the third strand of filament being woven between the first and second strands of filament in an alternating over-under pattern to form a continuous braided closed loop, wherein the first, second, and third strands of filament are each passed through one or more thru-holes formed in a surgical implant such that the continuous braided closed loop is coupled to the surgical implant.

15. The method of claim 14, further comprising actuating mechanical components associated with the mandrel to automatically repeat the steps of passing the first, second, and third strands of filament to increase a thickness of the continuous braided closed loop.

16. The method of claim 15, wherein operating mechanical components associated with the mandrel comprises rotating at least one roller to slidably move the first, second, and third strands of filament relative to the first, second, and third sets of posts.

17. The method of claim 15, wherein operating mechanical components associated with the mandrel comprises rotating the first, second, and third sets of posts to help move the first, second, and third strands of filament relative to the implant.

18. The method of claim 14, wherein the first, second, and third strands of filament are advanced circumferentially around the mandrel a plurality of times.

19. The method of claim 14, wherein the first, second, and third strands of filament are each passed through the same thru-holes formed in the surgical implant.

20. The method of claim 14, wherein the first strand of filament is passed through a different thru-hole than at least one of the second strand of filament and the third strand of filament.

* * * * *